United States Patent [19]
Matsumori

[11] Patent Number: 5,827,673
[45] Date of Patent: Oct. 27, 1998

[54] METHOD OF DETECTING MYOCARDIAL INFARCTION

[75] Inventor: Akira Matsumori, Minoo, Japan

[73] Assignees: Akira Matsumori, Osaka-Fu; Otsuka Pharmaceutical Co., Ltd., Tokyo-To, both of Japan

[21] Appl. No.: 696,160

[22] Filed: Aug. 13, 1996

[51] Int. Cl.⁶ ............... G01N 33/53; G01N 33/536; G01N 33/541; G01N 33/543
[52] U.S. Cl. ............... 435/7.92; 435/7.94; 436/536; 436/540; 436/548; 436/811; 436/815; 530/380; 530/403
[58] Field of Search ............... 435/7.92, 7.94; 436/536, 540, 548, 811, 815; 530/380, 403

[56] References Cited

PUBLICATIONS

Biochemical and Biophysical Research Communications, 221, 391–395 (1996).
Matsumori et al. Biochemical and Biophysical Research Communication 221(2):391–395, 1996.
Tsubouchi et al. Hepatology 13: 1–5, 1991.
Tomiya et al. Hepatology 15: 1–4, 1992.
Hara et al. Japanese Circulation Journal 58(7):588, 1994 58th Annual Scientific Meeting of the Japanese Circulation Society.

*Primary Examiner*—James C. Housel
*Assistant Examiner*—V. Ryan
*Attorney, Agent, or Firm*—Sughrue, Mion, Zinn, Macpeak & Seas, PLLC

[57] ABSTRACT

The present invention provides a method of detecting and diagnosing myocardial infarction which detects myocardial infarction by immunoassay using a monoclonal antibody having specific reactivity for human hepatocyte growth factor (HGF) as obtained by using human HGF as immunogen as well as a disganostic agent for myocardial infarction which comprises, as essential component thereof, the monoclonal antibody mentioned above. The method of the present invention makes it possible to detect and diagnose patients with myocardial infarction.

2 Claims, No Drawings

METHOD OF DETECTING MYOCARDIAL INFARCTION

TECHNICAL FIELD

The present invention relates to a method of detecting and diagnosing myocardial infarction using a monoclonal antibody against human hepatocyte growth factor in immunoassay and to a diagnostic agent for myocardial infarction to be used in said method.

BACKGROUND ART

The mechanism of acute myocardial infarction is presumably as follows: as the underlying morbid change, the atheroma disintegrates at a site of atherosclerosis relatively proximal to the coronary artery, the contents of the atheroma partially flows out into the blood vessel, whereby the intimal surface becomes unstable; thrombi are formed sequentially at the unstable sites and, in association with the originally occurring stenosis and relatively easily, they lead to luminal obstruction. It is also known that the above-mentioned thrombi, once formed, allows formation of $TXA_2$ (thromboxane $A_2$) at their sites, inducing, in turn, platelet aggregation and, on the other hand, causing spasm of the coronary artery. This vicious cycle is also considered as constituting an underlying morbid condition for the above-mentioned myocardial infarction or angina pectoris.

In these days, the above-mentioned myocardial infarction is treated in the CCU (coronary care unit), and the introduction of electrocardiographic monitoring and cardiopulmonary resuscitation and the application of antiarrhythmic agents and cardiac pacemakers, among others, are greatly contributing to reduce the acute phase morbidity among patients with said disease. Against acute heart failure accounting for most of deaths in said acute phase or against shock syndrome, as well, efforts have been made to develop more effective therapeutic means.

For more rational and more effective treatment of acute heart failure accompanying myocardial infarction and for maintaining and improving the cardiac function while preventing the progress of ischemia, it is necessary to correctly grasp the extent of hemodynamic disorder in each individual infarction case and, furthermore, care is required to select a proper therapeutic method according to the changing extent of lesion while monitoring the time course of myocardial lesion.

Since the incidence of coronary thrombosis among autopsied myocardial infarction cases remarkably varies from 21% to 97% among researchers, arguments had been made about the causal relation between both until recently. It is supposed that this be the result of differences, as a matter of course, with regard to study targets and methodology, in combination with gaps between myocardial infarction in the clinical sense and that morphologically confirmed by autopsy and, further, with the existence of various pathological types of infarction, among others.

However, recent development of positive clinical diagnostic means and therapeutic means for acute myocardial infarction is going to put an end to this debate. Thus, according to DeWood et al., clinical investigation by coronary angiographs and other means revealed coronary thrombosis in 73% of 517 cases of transmural myocardial infarction within 24 hours after attack, in 80% of cases within 6 hours after onset, in 59% of cases 6–12 hours after onset, and in 54% of cases 12–24 hours after onset. The importance of coronary thrombosis as a factor causative of myocardial infarction has thus been again recognized, inclusive of the appropriateness of wide application of thrombolytic therapy for coronary thrombosis.

After Karmen et al. reported for the first time in 1954 that increased serum levels of GOT (glutamic oxaloacetic transaminase), LDH (lactic dehydrogenase) and so forth are observed on the occasion of myocardial infarction, attempts were started to realize biochemical diagnosis by assaying substances discharged from necrotized myocardium into blood accompanying the onset of acute myocardial infarction, in particular by assaying enzymes escaping from the myocardium. Subsequently, increases of such enzymes as HBD ($\alpha$-hydroxybutyrate dehydrogenase) and CPK (creatine phosphokinase; international nomenclature: creatine kinase, CK) became known and are currently in wide use in clinical diagnosis.

For improved correctness of diagnosis and for severity estimation, however, further improvements are required. Thus, assaying of CPK-MB, which is a CPK isozyme, and the light chain of myosin, which is a structural protein, for instance is being put into practice.

GOT is an enzyme occurring most abundantly in heart and liver. It occurs also in skeletal muscle, kidney, pancreas, etc. An increase in GOT level is essential in the diagnosis of myocardial infarction but may pose the problem of differentiation from liver diseases. Its peak level appears after 12 to 30 hours and increased levels are observed for 3 to 5 days. However, since elevated levels of GOT are also observed in hepatitis cases, liver congestion cases and post-operative cases, the specificity of the diagnosis of myocardial infarction using this enzyme as an indicator is not high.

LDH occurs most abundantly in kidney and heart and is widely distributed also in skeletal muscle, erythrocyte, pancreas, spleen, liver, brain and lung. Therefore, there is the problem of differentiation from other diseases as in the case of GOT. Although, like GOT, the LDH level increases in not less than 90% of myocardial infarction cases, LDH occurs abundantly in liver, skeletal muscle and erythrocyte as well. This fact lowers the specificity, like the case of GOT.

Among LDH isozymes, HBD is a fraction showing high affinity for $\alpha$-hydroxybutyrate and is an enzyme almost identical to LDH1 and LDH2. It is highly specific to the myocardium. It is said that when the HBD/LDH ratio is 0.81 or above, the possibility of myocardial infarction is high.

CK occurs most abundantly in skeletal muscle and its content is also high in heart, brain, intestine and stomach but decreases in that order. It is contained little in liver, kidney and blood. Therefore, the use of this as an indicator can be considered as providing the most specific method of diagnosing myocardial infarction. It enables estimation of the size of infarct. Apart from diagnosis of myocardial infarction, increased CK levels are caused also by intramuscular injection, electric shock, surgery and cardiogenic shock, among others. In these cases, however, differentiation is possible if CK-MB, which is an isozyme of CK, is assayed.

Three isozymes, MM, BB and MB, are known of the above-mentioned CK. MM is specific to skeletal muscle, BB to brain, and MB to myocardium. In the myocardium, 10 to 40% of CK is CK-MB and the balance is CK-MM whereas, in the skeletal muscle, the proportion of CK-MB is 3% or less. It is said that when an increase in CK is observed in a human adult with a proportion of CK-MB of 5% or more relative to the total CK level, that CK-MB can be judged as derived from the myocardium.

Regrettably, however, it is known that different assay methods and different analyzers for assaying give significantly different CK assay results and that, in extreme cases, interlaboratory differences in assayed level amount to about 400% for one and the same sample. Therefore, it is an disadvantage that comparison cannot be made between values obtained in different laboratories.

As explained above, there is no method available as yet for detecting and diagnosing myocardial infarction in a simple and easy way and with more certainty. The advent of such a method of detection and diagnosis is awaited in the relevant field of art.

Accordingly, an object of the present invention is to establish such a method of detecting and diagnosing myocardial infarction as waited for in the relevant field of art.

As a result of intensive investigations, the present inventors found that when human hepatocyte growth factor (HGF) in patient's serum, for instance, is assayed using a monoclonal antibody specifically reacting with human HGF as obtained by using human HGF as immunogen, the measured HGF level satisfactorily reflects the state of myocardial infarction. The present invention was achieved based on these findings.

DISCLOSURE OF INVENTION

The present invention thus provides a method of detecting and diagnosing myocardial infarction which comprises detecting and diagnosing myocardial infarction by measuring the HGF level in the manner of immunoassay using a monoclonal antibody having specific reactivity for human HGF as obtained by using human HGF as immunogen.

The present invention also provides a diagnostic agent for myocardial infarction which comprises, as the essential component thereof, a monoclonal antibody having specific reactivity for human HGF as obtained by using human HGF as immunogen.

The present invention further provides a kit for detecting and diagnosing myocardial infraction which comprises, as the essential component thereof, a monoclonal antibody having specific reactivity for human HGF as obtained by using human HGF as immunogen.

The present invention makes it possible for the first time to detect and diagnose patients with myocardial infarction, and thus has a very high clinical value.

In the following, the monoclonal antibody to be used in accordance with the present invention and the immunoassay method using said antibody are described in detail.

The antibody to be used in the practice of the invention can be suitably selected from among monoclonal antibodies having specific reactivity for human HGF as obtained by using human HGF as immunogen. The human HGF to be used as immunogen is not limited to human-derived natural HGF but may be a genetically engineered recombinant HGF or an equivalent (fragment) of said natural or recombinant HGF which has a partial structure thereof. The above-mentioned human HGF to be used as immunogen further includes those products obtained according to the conventional immunogen producing technology by using the above-mentioned HGF or a fragment thereof as hapten and binding the same to a carrier by means of a binding reagent. These may be prepared by separate isolation from appropriate human cells or may be ones obtained from commercial or other sources.

The production of desired monoclonal antibodies using these as immunogens can be carried out, more particularly, by producing fused cells (hybridomas) from plasma cells (immunocytes) of a mammal immunized with the above-mentioned immunogen and mammalian plasmacytoma cells (myeloma cells), selecting a clone capable of producing a desired antibody (monoclonal antibody) which recognizes HGF, and cultivating said clone, for instance. Such monoclonal antibody production can be carried out basically in the conventional manner [see, for example, Hanfland, P., Chem. Phys. Lipids, 15, 105 (1975); Hanfland, P., Chem. Phys. Lipids, 10, 201 (1976); Koscielak, J., Eur. J. Biochem., 37, 214 (1978)].

The mammal to be immunized in the above production process is not limited specifically. Considering the amenability to fusion of its cells with the plasmacytoma cells to be used, however, mice, rats and the like are generally preferred. Immunization can be performed in the conventional manner, for example by administering the above-mentioned immunogen to the mammal by intravenous, intradermal, subcutaneous or intraperitoneal injection, for instance. More particularly, in the case of mice, for instance, the immunogen is diluted with phosphate-buffered saline (PBS) or physiological saline to an appropriate concentration, and administered to experimental animals several times at intervals of 2 to 14 days, in combination with a conventional adjuvant if desired, the total dose being preferably about 100 to about 500 μg/mouse. Usable as the adjuvant mentioned above are pertussis vaccine, complete Freund's adjuvant, alum, etc. Preferred as the immunocytes are splenocytes excised about 3 days after the last immunogen administration performed as mentioned above.

Useful as the mammalian plasmacytoma cells as the partner parent cells to be fused with the above-mentioned immunocytes are various known ones, for example p3/x63-Ag8 (X63) [Nature, 256, 495–497 (1975)], p3/X63-Ag8.U1 (P3U1) [Current Topics in Microbiology and Immunology, 81, 1–7 (1978)], P3/NSI-1-Ag4-1 (NS-1) [Eur. J. Immunol., 6, 511–519 (1976)], Sp2/0-Ag14 (Sp2/0) [Nature, 276, 269–270 (1978)], FO [J. Immunol. Meth., 35, 1–21 (1980)] and the like as well as murine myeloma cells such as 210.RCY3.Ag1.2.3. (Y3) [Nature, 277, 131–133 (1979)], among others.

Fusion reaction between the above-mentioned immunocytes and plasmacytoma cells can be carried out in the conventional manner, for example by the method of Milstein et al. [Methods in Enzymology, 73, 3 (1981)]. More particularly, the fusion reaction is generally carried out in a usual medium in the presence of a usual fusion promoter such as polyethylene glycol (PEG) or Sendai virus (HVJ). Where appropriate, an auxiliary agent such as dimethyl sulfoxide may further be added to the medium to improve the fusion efficiency. Such a technique as electric treatment (electrofusion) may also be suitably employed. The proportions of immunocytes and plasmacytoma cells are the same in the conventional methods. Thus, for example, immunocytes are generally used in a proportion of about 1 to 10 times relative to plasmacytoma cells. The medium for use in fusion reaction may be any of those generally used in proliferating the above-mentioned plasmacytoma cells, for example RPMI-1640 medium, MEM medium and other media commonly used in this kind of cell culture. It is generally recommended that these media be free of serum supplements such as fetal calf serum (FCS). Fusion is effected by blending well appropriate proportions of the above-mentioned immunocytes and plasmacytoma cells in the above medium and adding, to this mixture, a solution of PEG having an average molecular weight of, for example, about 1,000 to 6,000 as warmed beforehand to about 37° C. generally to a concentration of about 30 to 60 w/v %, followed by thorough mixing. Thereafter, centrifugation is repeated, each time following addition of an appropriate medium, to remove the supernatant. In this way, the desired hybridomas are formed.

The desired hybridomas obtained are separated by culturing in an usual selective medium, for example, HAT medium (medium containing hypoxanthine, aminopterin and thymidine). Generally, the culture in said HAT medium is carried out for a period of about several days to several weeks, namely a period sufficient to cause death of other cells (unfused cells etc.) than the desired hybridomas. The thus-obtained hybridomas are submitted to searching for the desired antibody and cloning by the ordinary limiting dilution method.

The search of the desired antibody-producing clones can be carried out by various methods generally used for antibody detection ("Hybridoma Technique and Monoclonal Antibodies", pages 30–53, published by Kabusiki Kaisha R&D Planning, Mar. 5, 1982), for example the ELISA method [Engvall, E. Meth. Enzymol., 170, 419–439 (1980)], plaque method, spot method, agglutination method, Ouchterlony method, radioimmunoassay (RIA) method, etc. The immunogen mentioned above can be used in this search.

The thus-obtained hybridoma which produces the desired monoclonal antibody recognizing HGF can be subcultured in an usual medium and can also be stored in liquefied nitrogen for a prolonged period of time. The monoclonal antibody can be collected as a culture supernatant by cultivating the above hybridoma in a usual manner or as ascitic fluid of a mammal which is amenable to the proliferation of the hybridoma by administering the hybridoma to the mammal. The former method is suited for producing high purity antibodies, while the latter is suited for large scale antibody production.

The antibody-producing hybridoma culture supernatant or mouse ascitic fluid obtained in the above manner can be used, as such, as a crude antibody solution and can also be purified in an usual manner, for example by ammonium sulfate fractionation, salting out, gel filtration, ion exchange chromatography, affinity chromatography such as protein A column chromatography, etc. A particularly preferred example of the above-mentioned monoclonal antibody is the one described in Japanese Patent Publication Hei 05-60359.

The immunoassay for detecting myocardial infarction in accordance with the present invention is now described in detail. This assay can be carried out in the manner of usual enzyme immunoassay by the sandwich technique, for instance, or in the manner of RIA, ELISA, agglutination assay or the like by the conventional competition, sandwich or other technique. The operational procedures and other details of these assay methods are as well known in the art.

Particularly, the three step sandwich method using the anti-HGF monoclonal antibody is highly sensitive, hence preferred. Typically, this method is carried out, for instance, in the following manner. Thus, the anti-HGF monoclonal antibody immobilized on an appropriate carrier such as a 96-well plate is used as the first antibody and is reacted with a standard HGF solution and a substance to be assayed (experimental sample or other sample) overnight at room temperature in a stationary state [first step], anti-HGF rabbit serum (rabbit anti-HGF polyclonal antibody) is then added, as the second antibody, to the above plate and said second antibody is allowed to react with the first step reaction product (reaction product from the monoclonal antibody and the substance to be assayed) at room temperature for about 2 hours [second step], and a fixed amount of a labeled antibody, such as enzyme-labeled anti-rabbit IgG antibody, is further allowed to react with the second step reaction product (reaction complex from the monoclonal antibody, the substance to be assayed and the second antibody) at room temperature for about 2 hours [third step]. Then, the unbound portion of the labeled antibody is separated and removed from the product of binding of the labeled antibody to said reaction complex as obtained in the third step, a color developer solution is added to the remainder for color reaction, the color reaction is stopped by adding 2N sulfuric acid, and the absorbance of the color reaction mixture obtained is measured. In this way, HGF in the sample can be assayed.

In the above procedure, each antibody employed can be immobilized (insolubilized) by binding the same physically or chemically to an insoluble carrier in a conventional manner. Examples of the carrier to be used for the above insolubilization are polystyrene, Sephadex, ion exchange resins, plastic tubes, amino group-containing copolymers, etc. The insolubilization can be effected by binding the antibody to the carrier chemically via covalent bonding using, for example, the diazo method, peptide method, alkylation method, the method using a crosslinking reagent or the method based on the Ugi reaction, or via ionic bonding using such a carrier as an ion exchange resin, or physically through adsorption on a porous glass carrier, for example glass beads.

The polyclonal antibody mentioned above is not limited to any particular species provided that it recognizes HGF. Thus, the antibody of the present invention or an antiserum produced in a mammalian body following administration, to the mammal, of the immunogen disclosed herein in relation to the production of the antibody of the present invention can be used. Said antiserum can be collected in a conventional manner.

The labeled antibody to be used as the label in the above-mentioned procedure may be any of known ones, for example labeled anti-immunoglobulin antibodies prepared by labeling those antisera already available on the market as obtained from immunized animals such as mice, rats, guinea pigs, rabbits, sheep, goats, horses, cattle, etc. with an enzyme such as peroxidase (POD), alkaline phosphatase, β-D-galactosidase, acid phosphatase, etc. More specifically, POD-labeled anti-rabbit IgG antibody, POD-labeled anti-mouse IgG antibody and the like can be used. This enzyme labeling can be effected in an usual manner.

In the detection method of the present invention, blood in the form of serum or plasma is preferred as the assay sample. In addition, cell tissue fluids, lymph, thymic fluid, ascitic fluid, amniotic fluid, gastric juice, urine, pancreatic fluid, bone marrow fluid, saliva and other various body fluids can also be used. The above-mentioned plasma may be citrated plasma, plasma containing EDTA or nafamostat mesilate, or the like.

In the above assay system, any of various conventional solvents inert to the reaction can be used. The use is preferred of a buffer having a pH value of about 5.0 to 9.0, for example citrate buffer, phosphate buffer, Tris-hydrochloride buffer or acetate buffer. In the practice of the present invention, it is more suited for the purpose of the above-mentioned detection method, hence recommendable, to add, to the above solvent, about 0.1 to 30 w/v % of serum (free of HGF which is the assay target) and/or about 0.1 to 2M NaCl.

The immune reaction conditions in the immunoassay are not particularly limited but may be the same as in conventional assay methods of this kind. Generally, the immune reaction can be carried out at a temperature not higher than about 45° C., preferably about 4° to 40° C., consuming a time of about 1 to 80 hours.

In the detection method of the present invention, the solid phase and liquid phase after completion of the immune reaction (product of binding of the labeled antibody to the reaction complex from the above-mentioned third step, and the unbound labeled antibody) can be separated from each other in an usual manner, for example by centrifugation, filtration, decantation or washing.

The enzyme label activity of each substance thus separated can be measured by any appropriate method selected from among various known methods according to the enzyme used. The color developer to be used on that occasion may be a conventional one. Thus, for example, o-phenylenediamine (OPD) can be used when the enzyme is peroxidase. The color reaction can be terminated in an usual manner, for example by adding an appropriate enzyme inhibitor, such as 1 to 4N sulfuric acid, to the reaction mixture.

Thus, according to the method of the present invention, HGF in samples can be assayed with high precision and high sensitivity by proceeding in a simple and easy way and, in this way, myocardial infarction can be detected.

The mean HGF level in healthy human subjects is 0.19±0.05 ng/ml, without any significant difference between both sexes. In fulminant hepatitis cases, the mean level is 10.17±24.77 ng/ml; in subacute hepatitis cases similar in diseased condition to "subacute type" fulminant hepatitis, the mean level is 2.71±2.52 ng/ml; and, further, the value is low in patients with acute hepatitis (0.40±0.16 ng/ml), chronic hepatitis (0.35±0.16 ng/ml), hepatic cirrhosis (0.60±0.35 ng/ml), hepatoma (0.56±0.36 ng/ml), etc. On the contrary, the results obtained in patients with myocardial infarction using the method of the present invention gave a value as high as 16.39±16.05 ng/ml and this value lasted about 15 hours; even after 2 days, the value was 1.91±1.72 ng/ml. This revealed that the method of the present invention can detect not only patients with myocardial infarction but also myocardial infarction cases after the lapse of a certain period of time following attack and that said method can be advantageously applied to the diagnosis and follow-up of myocardial infarction.

The present invention also provides a diagnostic agent for myocardial infarction which is suited for the above-mentioned immunoassay.

Said diagnostic agent comprises, as an essential component thereof, an anti-HGF monoclonal antibody and, in the case of the three step method mentioned above, for instance, it can further comprise a labeled antibody and a second antibody. In the monoclonal antibody reagent in said diagnostic agent, there may be further incorporated a stabilizer and/or preservative, such as glycerol or a bovine serum protein fraction. This antibody reagent is preferably in the form of a lyophilizate, and the diagnostic agent may contain a water-soluble or water-miscible solvent. Furthermore, a buffer solution for maintaining the reconstituted reagent system at a constant pH and/or a preservative and/or stabilizer for preventing deterioration of the sample may be added to the antibody reagent. A buffer solution capable of maintaining a pH of about 5.0 to 9.0 in carrying out the assay method of the present invention is preferably used. While the reconstituting agent preferably comprises water, part or the whole of said water may be replaced with a solvent miscible with water. Examples of the water-miscible solvent are glycerol, alcohols, glycol ethers, etc.

The following examples illustrates the present invention in further detail. They are, however, by no means limitative of the scope of the present invention.

A particularly preferred example of the above-mentioned immunoassay and diagnostic assay agent for detecting and determining myocardial infarction are described in Tsubouchi, et al. (Tsubouchi, H., et al., Hepatology, 13, 1–5 (1991)) and Tomiya, et al. (Tomiya, T., et al., Hepatology, 15, 1–4 (1992) as the specificity and sensitivity of the HGF assay kit for detecting any of hepatitis.

EXAMPLE 1

In 9 patients complaining chest pain lasting for 30 minutes or longer and judged as myocardial infarction based on an ST elevation of 0.1 mV or more in 2 or more leads in the electrocardiogram and on an increase in serum CPK, blood samples were collected at 3, 9, 15, 24 and 48 hours after onset of chest pain and the serum samples obtained were assayed for HGF as described below. For this assay, a kit described in the literature [Tsubouchi, H., et al., Hepatology, 13, 1–5 (1991); Tomiya, T. et al., Hepatology, 15, 1–4 (1992)] was used.

Thus, each well of 96-well antibody plates was washed three times by adding 350 µl of a washing solution to the well and the moisture was removed to a satisfactory extent by placing the plates on a paper towel. Then, 50 µl of phosphate buffer was added to each well, followed by further addition of 50 µl of the standard HGF solution or a sample prepared as mentioned above. After tight sealing with a sealant, the reaction was carried out at room temperature (25° C.) for 1 hour with shaking using a shaker. Thereafter, the postreaction liquid mixture was removed by suction and the well was washed 5 times with the washing solution. After washing, 100 µl of the first antibody (anti-HGF monoclonal antibody) was added to each well and, after tight sealing with a sealant, the reaction was carried out at room temperature (25° C.) for 1 hour with shaking using a shaker. Thereafter, the postreaction liquid mixture was removed by suction and the well was washed 5 times with the washing solution. After washing, 100 µl of the second antibody (anti-HGF polyclonal antibody, rabbit) was added to each well and, after tight sealing with a sealant, the reaction was carried out at room temperature (25° C.) for 1 hour with shaking using a shaker. Thereafter, the postreaction liquid mixture was removed by suction and the well was washed 5 times with the washing solution. After washing, 100 µl of the OPD substrate solution was added to each well and the reaction was carried out at room temperature (25° C.) for 10 minutes. The reaction was stopped by adding 100 µl of the reaction terminator solution to the reaction mixture and each well was measured for absorbance at the wavelength of 492 nm using a microplate absorbance reader.

The results thus obtained are shown below in Table 1.

TABLE 1

| Measurement | Serum HGF (ng/ml) | | | | |
|---|---|---|---|---|---|
| item | 3 hrs | 9 hrs | 15 hrs | 24 hrs | 48 hrs |
| n = 9 | 16.39 | 16.94 | 12.29 | 3.37 | 1.91 |
| Standard deviation | 16.05 | 11.80 | 12.23 | 2.41 | 1.72 |

It is evident from the above table that patients with myocardial infarction can be detected using the ELISA system in which the anti-HGF monoclonal antibody of the present invention is used.

EXAMPLE 2

Patients and Methods

Patients; We studied 27 consecutive patients with acute myocardial infarction.

Ten were women, and 17 were men, and mean age was 70±3 years (mean±SEM; range: 26–90). The average time from the onset of symptoms to admission was 7.6±1.3 hours (mean±SEM), with a range of 0.5 to 23 hours. The criteria for the selection of patients with acute myocardial infarction were precordial chest pain typical of cardiac ischemia lasting at least 30 minutes, ST elevation of at least 0.1 mV in two or more leads of ECG with subsequent evolution of ECG infarct pattern, and increased serum creatine kinase. All patients with acute myocardial infarction underwent routine cardiac catheterization. Patients admitted to the hospital within 24 hours after the onset of chest pain were included in this study. Twenty patients with stable angina pectoris were also studied. All patients with stable angina had typical exertional chest pain and there was no evidence of acute myocardial infarction as determined by a rise in serum creatine kinase or a new Q wave in ECG. We also studied 21 patients with dilated cardiomyopathy and 21 patients with hypertrophic cardiomyopathy in whom diagnosis was made as described previously (Matsumori. A., Yamada, T., Suzuki, H., Matoba, Y., and Sasayama, S., Br. Heart J. 72, 561–566 (1994)). Serum creatine kinase was measured using Rosalki method (normal values: 24–195 IU/L). HGF assay; Blood was collected at the time of admission from patients with acute myocardial infarction. Blood from other patients was collected after they had remained supine for at least 30 minutes in a quiet room. Blood was centrifuged and the separated serum was stored at −80° C. until assay; HGF was measured by the same method as Example 1.

Statistical methods. Mann-Whitney U-test was performed to compare the data for acute myocardial infarction with that for other heart diseases. Incidence of elevated levels of HGF and creatine kinase was compared by Fisher's exact test. Correlation between peak values of HGF and those of creatine kinase was analyzed by linear regression analysis. Data were expressed as mean±SEM.

Results

Serum HGF was below the detectable level in 3 of 20 patients with angina pectoris, 8 of 21 patients with dilated cardiomyopathy, and 8 of 21 patients with hypertrophic cardiomyopathy. Median values for HGF were 0.16 ng/ml in patients with angina pectoris, 0.14 ng/ml in those with dilated cardiomyopathy and 0.11 ng/ml in those with hypertrophic cardiomyopathy. Maximum levels of serum HGF in patients with angina pectoris and dilated and hypertrophic cardiomyopathy were 0.38, 0.30, and 0.24 respectively, and circulating HGF in these patients did not exceed the normal range of 0.39 ng/ml.

In contrast, 24 of 27 patients (89%) with acute myocardial infarction showed elevated serum HGF. Serum HGF was elevated 8 of 10 patients (80%) within 3 hours in patients with acute myocardial infarction after onset of chest pain (9.4±3.2 ng/ml, mean±SEM, range 0.25–24.7 ng/ml, n=10) and in 10 of 11 patients (91%) who admitted to the hospital between 6 and 9 hours after onset (11.0±2.6, 0.3–30.4 ng/ml, n=11), and in all those patients between 12 and 24 hours (13.1±5.7, 0.6–37.4 ng/ml, n=6). HGF levels were significantly higher in patients with acute myocardial infarction than in normal subjects or patients with other heart diseases throughout the examined time ($P<0.01$).

Abnormal creatine kinase values were detected in 2 of 10 patients (20%) within 3 hours (252±91, range 57–870 IU/L), and in 9 of 11 patients (82%) who admitted to the hospital between 6 and 9 hours after onset (1,218±453, 155–4,100 IU/L) and in all patients in those between 12 and 24 hours (2,802±1,143, 371–7,210 IU/L). Thus, frequency of elevated levels of HGF was significantly higher than that of creatine kinase within 3 hours after onset ($P<0.05$, Fisher's exact test). Linear regression analysis revealed a significant correlation between the HGF levels and levels of creatine Kinase ($y=150$ $x-428$, $r=0.87$, $P=0.002$).

In order to study whether skeletal muscle injury which may associate with cardiac catheterization results in increase of HGF, we measured serum HGF before and 24 hours after cardiac catheterization in 7 patients with angina pectoris. Serum HGF was not increased after catheterization (0.16±0.03 ng/ml versus 0.17±0.02 ng/ml).

In this study, markedly high levels of circulating HGF were noted in patients in the early period of acute myocardial infarction, and the elevated levels were comparable to or even higher than those in fulminant hepatic failure. However, none of the patients with acute myocardial infarction showed complication of hepatic or renal failure.

Moreover, serum levels of HGF were elevated in 80% of the patients as early as within 3 hours after onset of chest pain, whereas only 20% of the patients showed increased creatine kinase level during this period. Thus, elevated HGF levels appeared earlier than those of creatine kinase. The average value of 9.4 ng/ml within at 3 hours was 25 times greater than the maximum value seen in patients with other heart diseases (0.38 ng/ml), and 9 times greater than the maximum value of hepatic diseases (1.06 ng/ml), except for fulminant hepatic failure. Thus, measurement of serum HGF is more sensitive in the early diagnosis of acute myocardial infarction than creatine kinase.

High sensitivity of HGF measurement for detecting myocardial infarction within the early hours after the onset of symptoms will be a new biochemical marker for the diagnosis.

I claim:

1. A method of detecting acute myocardial infarction within three hours after onset thereof which comprises detecting myocardial infarction by measuring an HGF level of a patient by an immunoassay of a sample obtained within three hours after onset of said acute myocardial infarction to obtain a first measured value, said immunoassay using a monoclonal antibody having specific reactivity for human hepatocyte growth factor obtainable by using human hepatocyte growth factor as an immunogen and comparing said first measured value with those of healthy normal subjects and those of heart disease patients.

2. A method of diagnosing myocardial infarction within three hours after onset thereof as set forth in claim 1 which further comprises measuring the HGF level of a second sample, also obtained within three hours after onset of said myocardial infarction, to obtain a second measured value and comparing the measured values with those of healthy normal subjects and those of heart disease patients.

* * * * *